(12) United States Patent
Honeyman

(10) Patent No.: US 6,764,711 B1
(45) Date of Patent: Jul. 20, 2004

(54) PLANT TISSUE PRESERVATION METHOD AND SOLUTIONS

(76) Inventor: Peter J. Honeyman, 5529 SW. Patton Rd., Portland, OR (US) 97221

(*) Notice: Subject to any disclaimer, the term of this patent is extended or adjusted under 35 U.S.C. 154(b) by 0 days.

(21) Appl. No.: 09/975,698

(22) Filed: Oct. 10, 2001

Related U.S. Application Data

(60) Provisional application No. 60/239,737, filed on Oct. 11, 2000.

(51) Int. Cl.[7] .............................. B05D 1/38; B05D 3/00
(52) U.S. Cl. ..................... 427/4; 427/314; 427/316; 427/324; 427/407.1; 427/413; 427/430.1
(58) Field of Search ........................... 427/4, 314, 316, 427/324, 407.1, 413, 430.1, 180, 181, 242

(56) References Cited

U.S. PATENT DOCUMENTS

| | | | | |
|---|---|---|---|---|
| 2,658,836 A | * | 11/1953 | Fessenden | 427/4 |
| 3,563,780 A | * | 2/1971 | Waszkiewicz | 427/4 |
| 3,645,766 A | | 2/1972 | Mazzucato et al. | |
| 3,861,053 A | * | 1/1975 | Rovetti | 34/353 |
| 4,205,059 A | | 5/1980 | von Hagens | |
| 4,244,992 A | | 1/1981 | von Hagens | |
| 4,272,571 A | * | 6/1981 | Romero-Sierra et al. | 428/24 |
| 4,278,701 A | | 7/1981 | von Hagens | |
| 4,808,447 A | | 2/1989 | Baker | |

* cited by examiner

Primary Examiner—Shrive P. Beck
Assistant Examiner—Jennifer Kolb Michener
(74) Attorney, Agent, or Firm—Karen Dana Oster

(57) ABSTRACT

A process generally for preserving fresh-cut flowers and plant tissue, particularly fitted for fresh-cut flowers and plant tissue for use in manufacturing applications to form permanently flexible high-wear products to be used in a wide range of temperature and humidity conditions.

A method for preserving the plant tissue wherein the plant tissue is formed and substantially dehydrated, whereupon the plant tissue is subsequently saturated with a saturating mix, removed from the saturating mix, drained, dried, and then subsequently coated with a coating mix, removed, drained, and dried. An optional polishing mix may be applied for cosmetic purposes. The finished product retains the integrity of the original flower in shape, texture, size, and color and is highly flexible and durable under conditions of constant physical wear and disturbance.

15 Claims, 6 Drawing Sheets

PLANT TISSUE PRESERVATION METHOD AND SOLUTIONS

The present application is based on, and claims priority from, provisional application serial No. 60/239,737, filed Oct. 11, 2000, and is hereby incorporated herein by reference.

BACKGROUND OF INVENTION

The present invention is directed generally to a method of and solutions for preserving fresh-cut flowers and plant tissue and more specifically for preserving fresh-cut flowers and plant tissue for use in manufacturing applications to form permanently flexible high-wear products to be used under a wide range of temperature and humidity conditions.

Fresh flowers have been worn as accessories for many centuries, but recent trends in the fashion world have dictated the increased use of flowers also as attachments to and accessories for such items as shoes, jewelry, purses, giftware, ornaments, picture frames, corsages, bouquets, scripts, hair clips, barrettes, and shadow boxes (collectively, "floral accessories"). But extending the lifetime of fresh-cut flowers has never progressed beyond saving the fresh-cut flowers for a few short days. As a result, using fresh-cut flowers in the floral-accessory business has been impractical. It is not realistic for manufacturers to use fresh flowers in floral-accessory applications requiring long-term wear and use. Instead, manufacturers have responded to the demand for floral accessories by creating faux flowers, using materials such as silk, plastic, rubber, beads, metal, ceramics, paper, leather, and fabric. While these materials are able to withstand the normal wear and tear of daily use, they nonetheless lack the beauty and authenticity of real flowers.

There are a considerable number of references relating to various methods of preserving flowers, plant and animal biological material, leaves, and vegetables (collectively, "natural materials"). These references include U.S. Pat. No. 2,658,836 to Fessenden; U.S. Pat. No. 3,563,780 to Waszkiewicz; U.S. Pat. No. 3,645,766 to Mazzucato; U.S. Pat. No. 3,861,053 to Rovetti; U.S. Pat. Nos. 4,205,059, 4,244,992, and 4,278,701 to von Hagens; U.S. Pat. No. 4,272,571 to Romero-Sierra et al: and U.S. Pat. No. 4,808,447 to Baker. The references are generally concerned with the preservation of natural materials for educational uses, such as studies in the natural sciences (including detailed botanical, medicinal, or industrial observation), or for commercial uses (including visual and aesthetically pleasing displays in which the materials retain a long-lasting, lifelike, and natural appearance). The references are not concerned with the suitability of the final preserved natural materials for manufacturing and therefore do not deal with the preserved natural materials' ability to withstand flexing and physical handling on a daily basis.

Many of the references disclose dehydrating processes, including but not limited to placing natural materials in chemical solutions; burying natural materials in dry, absorbent, granular, or powdered substances; or freezing the natural materials. The purpose of the dehydrating process is to prevent decomposition, preserve color, and preserve the integrity of shape and texture. But these dehydrating processes leave the natural materials in a highly delicate condition, brittle and difficult to use. For strengthening purposes, most of the references disclose that the dehydrated natural materials are subsequently subjected to various preservation treatments, which include being embedded in or impregnated or coated with waxes, oils, glycerin, polymers, or resins to strengthen the dehydrated natural materials and ultimately make the preserved natural materials practical for whatever purpose is intended.

Many of the references describe the results of the various dehydration and preservation processes as leaving the natural materials in conditions varying from "solid" or "more rigid" than the original natural material to "flexible," "durable," and "appearing to be alive." These are, however, relative and subjective terms that are not measurably defined.

None of the references, however, are directed to the preservation of natural materials so that the natural materials can be used in a variety of changing, diverse, and climatic conditions, such as moving from warm and moist conditions to cold and dry conditions (e.g., from going indoors to outdoors, to and from air-conditioned or humid environments, or from one to another distinctly different climate zone, such as from Arizona to Hawaii or from Florida to Alaska). These kinds of changes can adversely affect the performance and appearance of the natural materials mentioned in the references.

For example, the natural materials are generally hygroscopic and thus influenced by varying humidity. A hygroscopic flower will absorb moisture slowly, subsequently increasing the weight of the flower. Thus, and particularly if the flowers have petals with a large surface area in relation to the part of the petal that attaches to the stem (e.g., an orchid), upon absorption of moisture and the consequential weight increase, the petals will droop and the flower will be unable to retain its original integrity and shape. The absorption of moisture will eventually cause decomposition of the flower.

Further, the preservation treatments that leave the natural material nonhygroscopic are not suitable for manufacturing purposes because the natural material becomes too brittle or delicate for use. In many of the preservation treatments that render the natural materials nonhygroscopic, preservatives or artificial coloring must be added or applied to replace or overcome a loss of natural coloring.

While many of the references provide for natural materials to be treated for display or observation, none of the references cause the preserved natural materials to be resilient and flexible enough for making into and using as floral accessories. Nor were such preserved natural materials designed to withstand the rigors of daily wear, which at times may be not so much "use" as "abuse."

U.S. Pat. Nos. 4,278,701, 4,244,992, and 4,205,059 to von Hagens generally describe a curing process for converting a wide variety of human and other animal tissue to durable, solid objects retaining all the features of interest to the student of anatomy or histology. These references disclose both methods for preparing a body consisting essentially of animal or vegetal tissue, and human or animal tissues prepared by the methods disclosed. These references generally disclose replacing the water content of a water-bearing tissue with an organic solvent volatile in a vacuum at ambient temperature, holding the water-bearing tissue in contact with a fluid precursor until the organic solvent is volatilized and replaced in the water-bearing tissue by the fluid precursor, the precursor being capable of being polymerized into a solid, water-insoluble, synthetic resin, and holding the tissue under polymerization conditions until the fluid precursor is cured into a solid resin.

BRIEF SUMMARY OF THE INVENTION

This invention comprises methods and compositions for the permanent preservation of plant tissue, such as fresh-cut flowers, in such a manner as to retain the original size, form, color, and texture of the plant tissue. This invention more specifically comprises using the preserved plant tissue in manufacturing applications to form permanently flexible high-wear products, including jewelry, accessories, hair clips, barrettes, attachments to clothing, attachments to accessories, and displays.

In a first preferred embodiment of this invention, the plant tissue is saturated, coated, and subsequently manufactured into a wide range of high-wear fashion jewelry and personal accessories, including but not limited to giftware and ornaments.

A second preferred embodiment of this invention includes a method for preserving plant tissue by dehydrating the plant tissue, and subsequently saturating the plant tissue with a saturating mix. If desired, the preserved plant tissue may be subsequently used in high-wear applications.

A third preferred embodiment of this invention includes a method for the preservation of plant tissue by which the plant tissue is formed in such a way that the original shape and volume of the tissue is substantially maintained. The plant tissue is subsequently dehydrated and then saturated with a saturation mix until the plant tissue is fully saturated. If desired, a coating mix is then applied to the plant tissue, thereby creating a flexible and pliable plant tissue that displays substantial elasticity and bends freely under pressure; essentially a rubberized plant tissue.

A fourth preferred embodiment of this invention is a method for the preservation of plant tissue by which the plant tissue is formed and subsequently dehydrated. Preferably, the plant tissue is then cleaned so that all by-products of the dehydration process are removed. Saturation and coating mixes are then applied to the plant tissue in the manner set forth above, and then a polishing mix is applied to the plant tissue, which protects and provides an aesthetically pleasing gloss to the plant tissue.

In all the preferred embodiments, the plant tissue is preserved so that the plant tissue gains substantial elasticity, becoming so flexible and pliable that the plant tissue bends freely under pressure.

The foregoing and other objectives, features, and advantages of the invention will be more readily understood upon consideration of the following detailed description of the invention, taken in conjunction with the accompanying drawings.

DETAILED DESCRIPTION OF THE INVENTION

Figure 1:
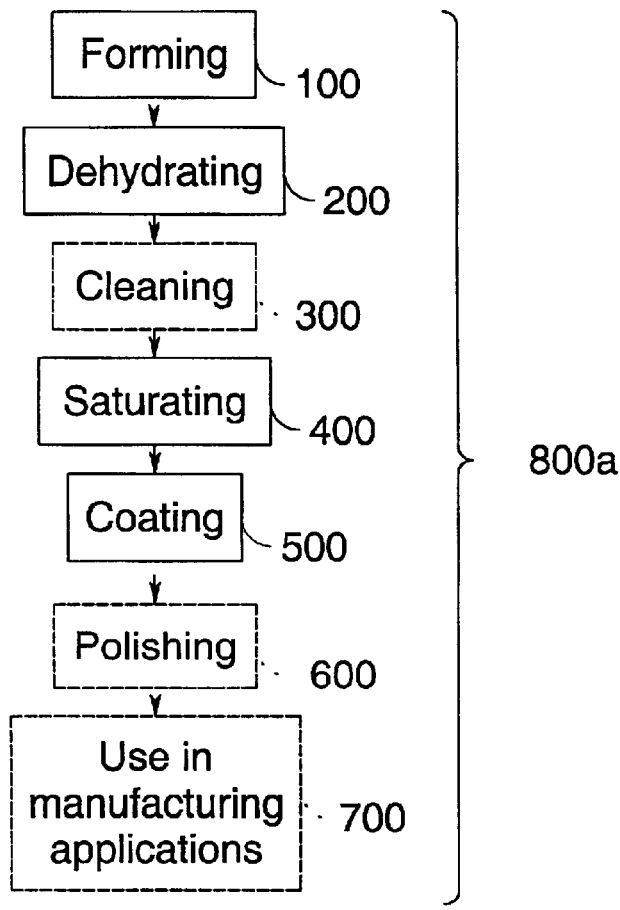
FIG. 1 is a flowchart illustrating a first preferred embodiment of a plant tissue preservation process of the present invention.
Figure 2:
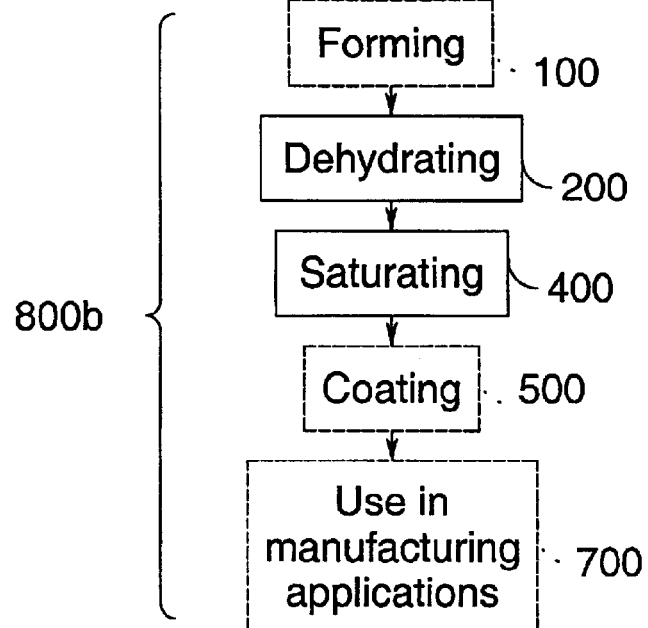
FIG. 2 is a flowchart illustrating a second preferred embodiment of the plant tissue preservation process of the present invention.

FIG. 1 and FIG. 2 show two preferred embodiments of the present invention. FIG. 1 shows a first preferred embodiment of a plant tissue preservation process 800a. FIG. 2 shows a second preferred embodiment of a plant tissue preservation process 800b. The methods 800a, 800b shown in these figures are exemplary preservation processes and are not the exclusive methods used to complete the invention.

Figure 3:
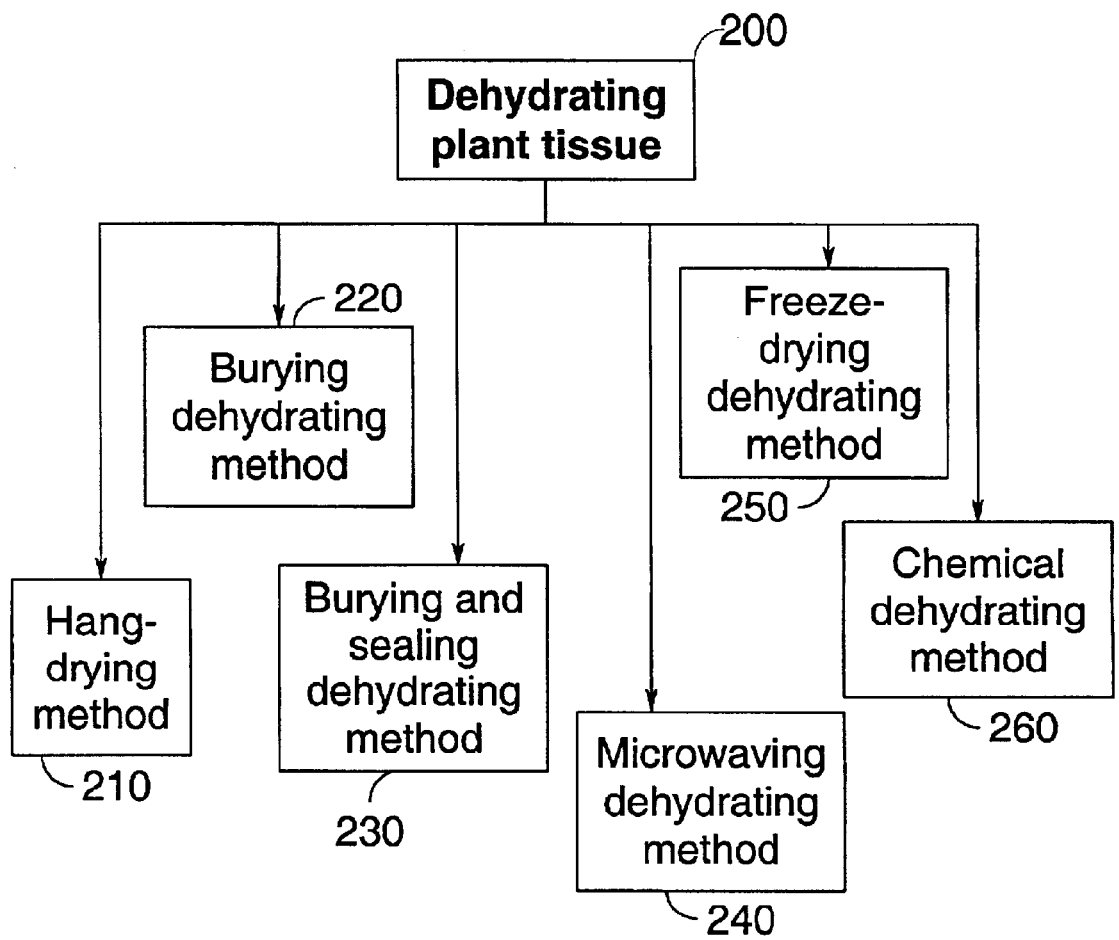
FIG. 3 is a flowchart illustrating exemplary methods of dehydrating the plant tissue.
Figure 4:
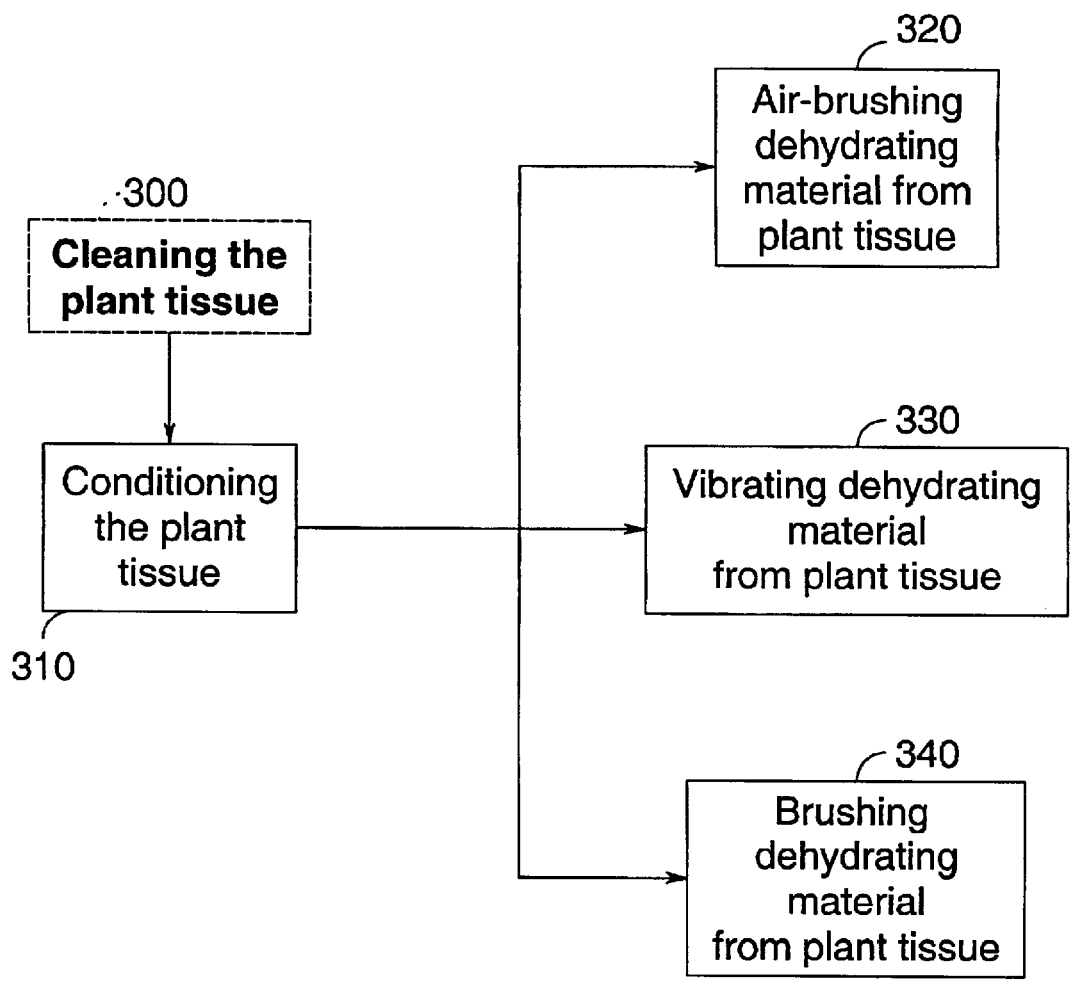
FIG. 4 is a flowchart illustrating exemplary methods of cleaning the plant tissue after the dehydration process.
Figure 5:
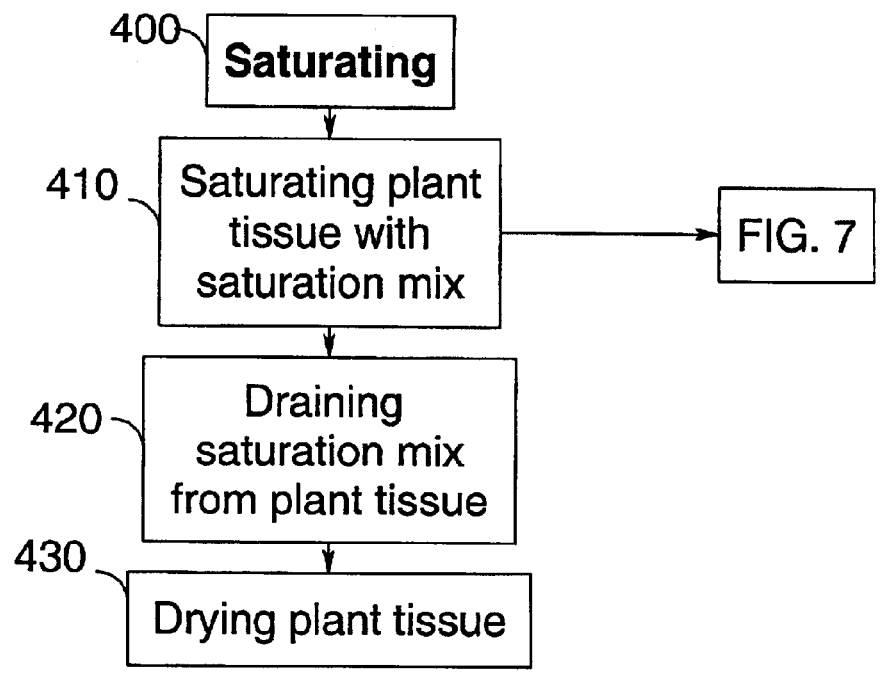
FIG. 5 is a flowchart illustrating an exemplary method for saturating the plant tissue in the saturation mixes.
Figure 6:
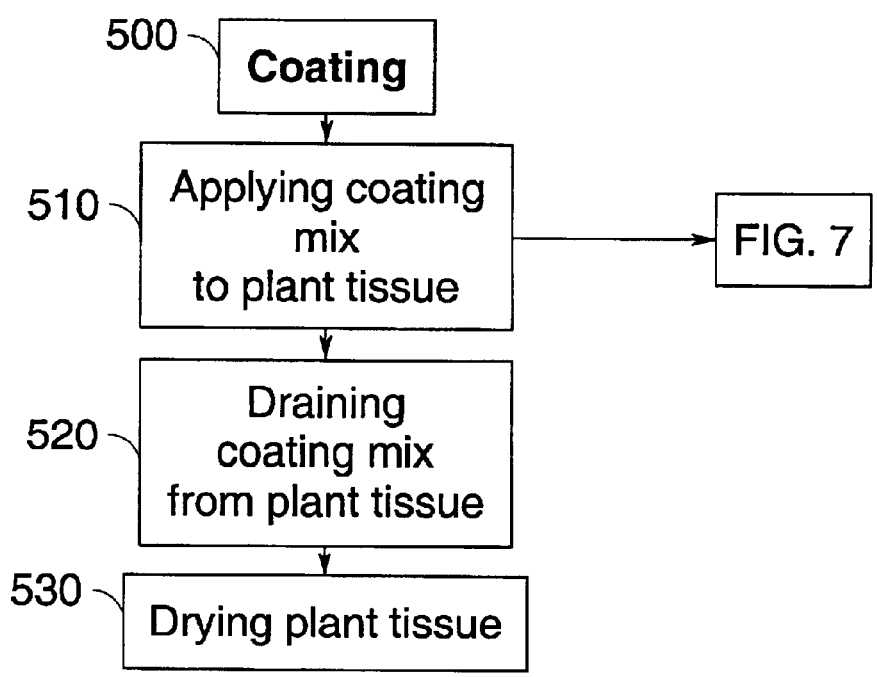
FIG. 6 is a flowchart illustrating an exemplary method for coating the plant tissue in the coating mixes.
Figure 8:
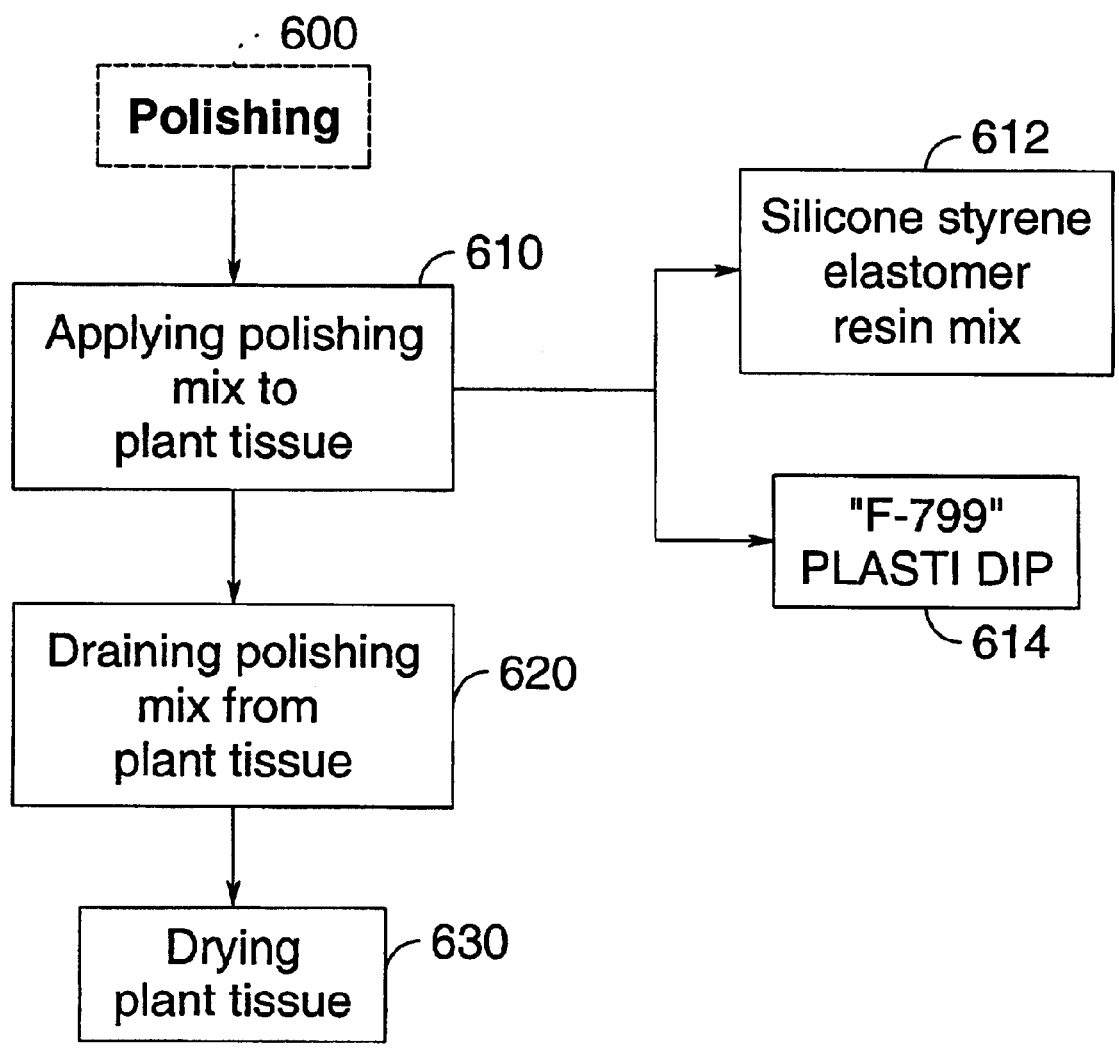
FIG. 8 is a flowchart illustrating an exemplary method for polishing the surface of the plant tissue, including alternative solutions that may be used to complete the method.

FIG. 1 shows a first preferred embodiment of the plant tissue preservation process 800a. The first step is the formation of the plant tissue 100. The second step is the dehydration of the plant tissue 200 (FIG. 3). The-optional third step is the cleaning of the plant tissue 300 (FIG. 4). The fourth step is the saturation of the plant tissue 400 (FIG. 5). The fifth step is the coating of the plant tissue 500 (FIG. 6). The sixth optional step is the polishing of the surface of the plant tissue 600 (FIG. 8). The seventh optional step is the use of the plant tissue in manufacturing applications 700 such as those used to create floral accessories or other items for use in high-wear applications. These steps may be performed in alternate orders, additional steps may be included and other steps excluded.

FIG. 2 shows a second preferred embodiment of the plant tissue preservation process. The optional first step is the forming of the plant tissue 100. The second step is the dehydration of the plant tissue 200 (FIG. 3). The third step is the saturation of the plant tissue 400 (FIG. 5). The optional fourth step is the coating of the plant tissue 500 (FIG. 6). The optional fifth step is the use of the plant tissue in manufacturing applications 700 such as those used to create floral accessories or other items for use in high-wear applications. These steps may be performed in alternative orders, and additional steps may be included, and other steps may be excluded.

The steps of the methods 800a and 800b will be discussed individually below.

The forming step 100 shown in FIGS. 1 and 2 is used to mold and shape the plant tissue into its natural shape. The forming step 100 may be optional if using the chemical dehydrating method, freeze-drying dehydrating method, or hang-drying dehydrating method in the dehydrating step 200.

One exemplary method for forming the plant tissue is the setting method, although other forming processes known to persons having ordinary skill in the art will also satisfy the forming step 100.

In the setting method, the plant tissue is set carefully in a container upon approximately one half of an inch of dehydrating materials, which may include granulated dry silica gel, powdered dry silica gel, borax, free-flowing flour, sand, powdered glass, and any other granular material that is absorbing (collectively "dehydrating materials"). After the plant tissue is shaped within the container into its preferred shape, additional dehydrating materials should be carefully packed around the plant tissue, with care being given not to damage the shape of the plant tissue. The dehydrating material is packed in the container around the plant tissue until the dehydrating material fully surrounds and envelopes the plant tissue.

If forming a large amount of plant tissue, it is advantageous to separate the plant tissue within the container so that the various plant tissues are not in contact with each other. If stacking the plant tissue, it is preferred that there be approximately one half of an inch of dehydrating material placed between each layer to ensure enough absorbent material to permit absorption of essentially all of the moisture by the dehydrating materials used in the subsequent dehydrating step.

The setting method is preferred when the preferred dehydrating step 200 will be either the burying and sealing dehydrating method 230, the burying dehydrating method 220, or the microwaving dehydrating method 240, with all such methods being defined below.

The dehydrating step 200 shown in FIGS. 1 and 2 may be performed by several dehydrating methods (FIG. 3). Whichever dehydrating method is chosen, its purpose is to dehydrate the plant tissue so that essentially all of the moisture is removed from the plant tissue. If the plant tissue has previously been dehydrated, the dehydrating step 200 will not be necessary for purposes of this invention.

FIG. 3 shows several exemplary methods for dehydrating the plant tissue, including an air-drying method 210, in which the plant tissue is hung upside down; a basic burying dehydrating method 220, in which the plant tissue is buried in dehydrating materials; a burying and sealing method 230, in which the plant tissue is buried in dehydrating materials and sealed in a container; a microwaving dehydrating method 240, in which the plant tissue is microwaved in dehydrating materials; a freeze-dying dehydrating method 250, in which the plant tissue is freeze-dried; and a chemical dehydrating method 260, in which chemical solutions are used to dehydrate the plant tissue. Other dehydrating processes known to persons having ordinary skill in the art will also satisfy the dehydrating step 200.

The first exemplary method for dehydrating the plant tissue is the hang-drying method 210, in which the plant tissue is hung upside down in ambient conditions until the moisture content of the plant tissue is essentially removed. No expediting factors are used in this method.

The second exemplary method for dehydrating the plant tissue is the basic burying dehydrating method 200, in which the plant tissue, having previously been formed and packed in the container by the above stated setting method, is placed in a hot room for a sufficient amount of time for the dehydrating material to fully absorb essentially all of the moisture remaining in the plant tissue.

If dry silica gel is used as the dehydrating material in the basic burying dehydrating method 120, it is preferred that the dry silica gel be no larger than a grain of table salt. Although other grain sizes may be used, the soft, fine grain reduces the risk of permanently impressing pockmarks onto the outer skin of the plant tissue.

The third exemplary method for dehydrating the plant tissue is the burying and sealing dehydrating method 230, in which the plant tissue is buried and sealed in dehydrating materials. Having previously been formed by the above stated method, the plant tissue is sealed in a container and placed in ambient conditions for a time sufficient for the dehydrating material to essentially absorb all of the remaining moisture within the plant tissue. No expediting factors are used in this method.

In a preferred embodiment, the time needed to dehydrate the plant tissue using the burying and sealing dehydration method 230 will be approximately between 3 to 7 days. However, in order to ensure proper dehydration of the plant tissue, the time will likely need to be varied based upon the moisture quantity of the plant tissue, the type of dehydrating material being used, and the outside temperature surrounding the container.

It is preferred that the container in the burying and sealing dehydrating method have an air-tight lid which, when sealed, will prevent interaction of the dehydrating materials with any moisture outside the container which could prevent proper dehydration of the plant tissue.

The fourth exemplary method for dehydrating the plant tissue is a nmicrowaving dehydrating method 240, in which the plant tissue, having previously been formed and packed into a container by the aforementioned setting method, is placed in a microwave oven and heated for a specified time. The heating time of the plant tissue will vary depending on a variety of factors, such as the power of the oven, the quantity of plant tissue, the moisture content of the plant tissue, and the volume and moisture content of the dehydrating material.

In the microwaving dehydrating method 240, it is advantageous to use a microwave oven having an internal rotating device that rotates the container on a centralized axis within the microwave oven. Using a microwave oven with an internal rotating device increases the chances of complete and even dehydration of the plant tissue. A microwave oven without an internal rotating device may also be used, but if the microwave oven has no internal rotating device, it is preferred that the container be manually rotated 90 degrees every quarter of the total heating time, so that all four sides of the container are heated equally.

After being heated in the microwave oven, the container is removed and allowed to cool to room temperature. This cooling period is by natural dissipation of heat under ambient conditions without the application of any cooling methods to accelerate the cooling process.

One advantage of using the microwaving dehydrating method 240 for dehydrating the plant tissue is that the time required to dehydrate the plant tissue is significantly shortened. Further, the microwaving dehydrating method 240 tends to more accurately preserve the color, color intensity, texture, and particularly the strength of the original plant tissue. This method is preferred particularly for orchids and plant tissues where the petals are attached to the stem at a relatively narrow location.

A fourth exemplary method of dehydrating the plant tissue is a freeze-drying method 250. The freeze-drying process 250 is commonly known to persons having ordinary skill in the art. U.S. Pat. No. 4,312,134 to Strausser, incorporated herein by reference, is a Method of Freeze-Drying Flower Arrangements and shows one exemplary method of freeze-drying.

A fifth exemplary method of dehydrating the plant tissue is a chemical dehydrating method 260, in which the plant tissue is dehydrated by various chemical solutions commonly known to persons having ordinary skill in the art.

The optional cleaning step 300 detailed in FIG. 4 may be performed by a variety of different methods. Whichever cleaning method is chosen, its purpose is to remove any remaining dehydrating materials from the plant tissue. All plant tissue should be treated with extreme caution and with the awareness that the dehydrating step 200 may have left the plant tissue delicate, brittle, and fragile.

If the plant tissue is in a brittle, delicate state after being dehydrated, it is advantageous to condition 310 the plant tissue by leaving the plant tissue in ambient conditions for a period of time sufficient for the plant tissue to absorb moisture and become less brittle. Generally, a period of approximately 24 hours is sufficient for the conditioning process 310. The absorption of moisture will make the plant tissue less brittle, and remaining dehydrating materials will be more easily removable. After the dehydrating materials are removed by any of the cleaning processes set forth below, it is preferred that the plant tissue be returned to a hot dry room or container for a period of time sufficient for the plant tissue to essentially lose all of the moisture it may have absorbed during the conditioning process. It is preferred that the plant tissue be retained in the aforementioned conditions until the next process is applied.

The cleaning step 300 is advantageous if residual compounds from the dehydrating materials remain on the plant tissue. If no dehydrating materials remain on the plant tissue, or if the plant tissue was previously dehydrated before beginning this invention, this step is unnecessary. It should be noted that a cleaning step similar to the cleaning steps detailed below may be done prior to the dehydrating step 200 in addition to or as an alternative to the cleaning step 300. Similarly, it should be noted that additional cleaning steps may be added throughout the invention.

FIG. 4 details several exemplary methods that may be used to clean the a plant tissue, which include air-brushing the plant tissue 320, vibrating the plant tissue 330, or brushing the plant tissue with a brush 340. Other cleaning processes known to persons having ordinary skill in the art will also satisfy the cleaning step 300.

The first exemplary method of cleaning the plant tissue is air-brushing the plant tissue 320 using methods commonly employed by persons having ordinary skill in the art. Generally, a jet of air is pushed onto the plant tissue, thereby removing the dehydrating materials from the plant tissue. The air-brushing method 320 is preferred for use with plant tissue that has been dehydrated according to the burying and sealing dehydrating method and the basic burying dehydrating method.

The second exemplary method of cleaning the plant tissue is vibrating, shaking or agitating (collectively "vibrating") the plant tissue 330 until all remaining dehydrating materials have been removed. The vibrating method 330 is preferred for use with plant tissue that has been dehydrated according to the burying and sealing dehydrating method and the basic burying dehydrating method.

The third exemplary method of cleaning the plant tissue is brushing the plant tissue 340 to remove the remaining dehydrating materials. It is preferable that a small, dry, soft paintbrush or makeup brush be used to prevent damage to the plant tissue. The brushing method 340 is preferred for use with plant tissue that has been dehydrated according to the burying and sealing dehydrating method, the basic burying dehydrating method, or the microwaving dehydrating method.

FIG. 5 shows an exemplary method for saturating the plant tissue 400. The purpose of this step is for the saturation mix, or mixes, as shown in FIG. 7, and described individually below, to penetrate the fibers of the plant tissue, thereby ensuring the durability and permanent flexibility of the plant tissue.

In a preferred method, the plant tissue is saturated with the saturation mix 410 long enough for the saturation mix to essentially penetrate all of the fibers of the plant tissue. The saturation time will vary according to the condition of the plant tissue, including the resistance of the plant tissue to the saturation mix and the delicacy of the plant tissue. But even if the saturation mix is applied to the plant tissue for an extended time, there will be no further change in the condition of the plant tissue.

The plant tissue can be saturated by the saturation mix 410 through immersion of the plant tissue into the saturation mix, application of the saturation mix to the plant tissue, or any other method which will ensure essentially full saturation of the plant tissue with the saturation mix (collectively "saturation methods").

Figure 7:
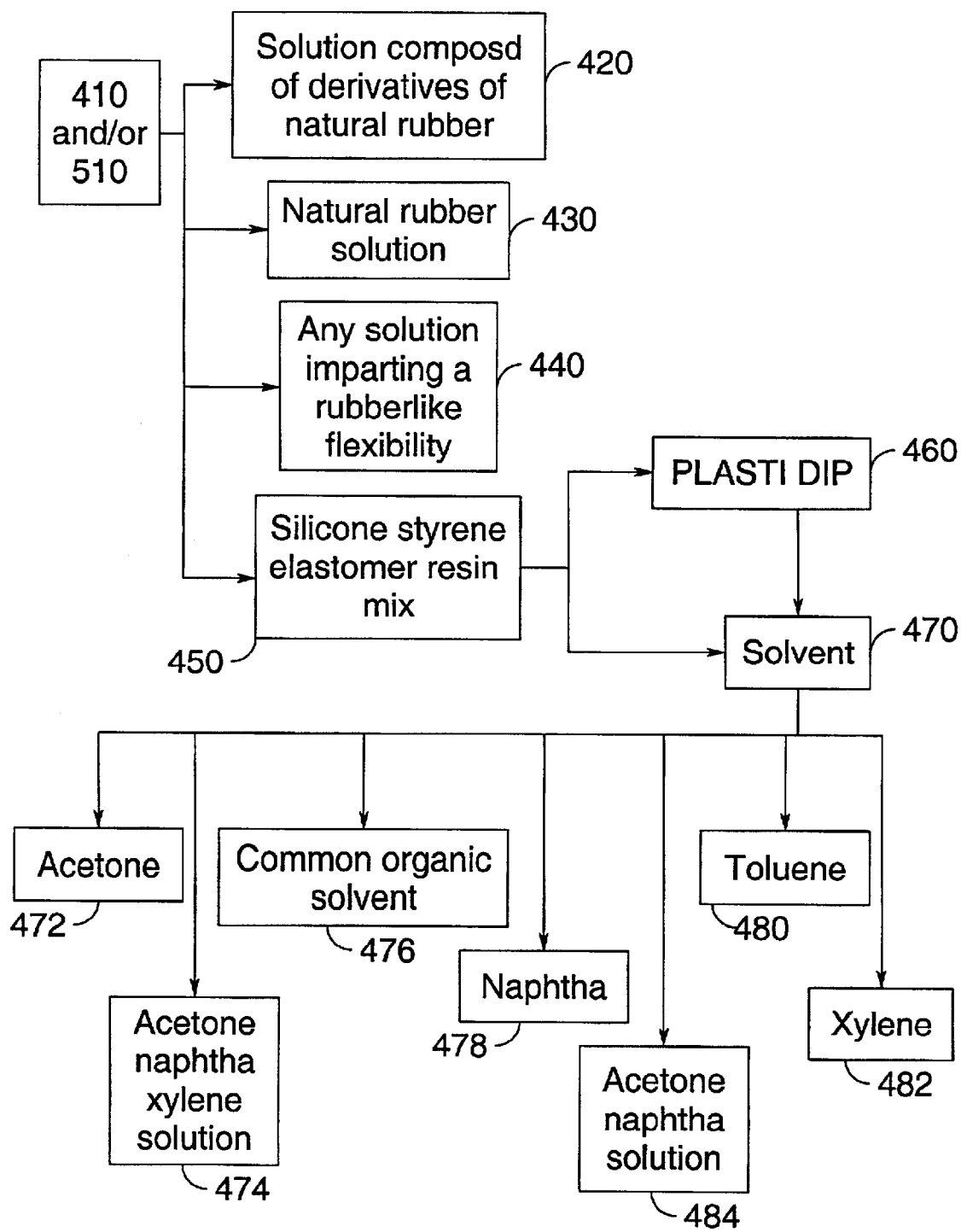
FIG. 7 is a flowchart illustrating exemplary saturating and coating mixes that may be used to complete the exemplary methods for saturating and coating the plant tissue.

FIG. 7 shows various solutions that may be used as the first saturation mix, including any solution composed of derivatives of natural rubber 420, a natural rubber solution 430, a solution that imparts a rubber-like flexibility 440, or a silicone/styrene elastomer resin mix 450 with solvent 470 solution (collectively, "saturation mixes").

In a preferred embodiment of the saturation mix, the saturation mix is composed of a silicone/styrene elastomer resin mix 450 and solvent 470 solution. It is preferred that the resins used in the silicone/styrene elastomer resin mix and solvent solution be block (or graft) copolymers. These copolymers may be composed of dimethylsiloxane and polystyrene (collectively, "copolymers"). These copolymers may be mixed separately or in combination with a rubber vulcanizing agent, which makes the plant tissue stronger, more flexible, stretchable, and elastic; a UV stabilizer, which limits the effects of light thereby hindering and protecting against color degradation; or an antioxidant, which inhibits the regeneration and subsequent breakdown of the saturation mix.

In using the silicone/styrene elastomer resin mix and solvent solution, it is a first preferred embodiment that the silicone predominate over the styrene. Upon drying, the silicone/styrene elastomer resin mix and solvent solution in which the silicone predominates over the styrene generally exhibit characteristics such as extreme flexibility, and little or no chemical cross-linking, chemical curing, or polymerization.

In a second preferred embodiment of the silicone/styrene elastomer resin mix and solvent solution, the silicone/styrene elastomer resin mix-to-solvent ratio is approximately 1:1.5, being one part of the silicone/styrene elastomer resin mix 450 to one and a half parts of solvent 470.

If desired, the silicone/styrene elastomer resin mix 450 of the saturation mix can be either PLASTI DIP® or PLASTI DIP® UV STABLE (collectively, "PLASTI DIP®" 460), both made by PLASTI DIP® International of St. Paul, Minn. The PLASTI DIP® 460 solution is mixed at the consistency supplied directly by the manufacturer, along with a solvent 470. It is preferred in preparing the solvent and PLASTI DIP® solution, that the solution be thoroughly mixed so that air bubbles are removed from the solution before saturation of the plant tissue 410.

Solvents 470 to be mixed with the silicone styrene elastomer resin mix 450, including PLASTI DIP® 460, may include acetone 472, naphtha 478, toluene 480, xylene 482, or any common organic solvent 476, that is suitable to be combined with the rubberizing solution (collectively, "solvents"). These solvents may be used individually, or the solvents may be mixed together to form a solvent solution. For example, in a first preferred embodiment, the solvent 470 used may be a solvent solution comprising xylene, acetone, and naphtha 474 as provided by PLASTI DIP®. In a second preferred embodiment, the solvent used may be a solvent solution comprising acetone and naphtha 484, said acetone and naphtha solvents being thoroughly mixed together before being combined with the silicone styrene elastomer resin mix 450, including PLASTI DIP® 460.

After saturating the plant tissue 410 with the saturation mix, it is preferred that the plant tissue be removed from the saturation mix and placed so that excess fluid still remaining and draining off the plant tissue pours, drips, or slides to the base of the plant tissue 420. This is advantageous because it helps reinforce the weaker areas of the plant tissue and in flowers prevents petals from falling off under conditions of extreme flexing. In particular, with orchids and flowers of similar physical construction, the draining of the solution as it dries is preferable because it helps reinforce the area of the petal that joins the stem to the flower. This step strengthens the small joints and connections of the flower against conditions of flexing, both from the external coating on the plant tissue and from within, because the saturating solution will be partially or fully absorbed into the plant tissue. This helps the plant tissue to withstand manufacturing processes. After the excess saturating solution is drained from the plant tissue 420, the plant tissue is then left to dry 430.

In a preferred method of draining 420 and subsequently drying 430 the plant tissue, the plant tissue is placed on a rack to drain in the above stated manner, and routinely moved to different positions on the rack to ensure that the saturation mix doesn't dry and stick to the rack.

After the saturation mix has fully dried, a coating mix may be applied 510 to the plant tissue as shown in FIG. 6. The coating step 500 strengthens the outer part of the plant tissue, thereby allowing the plant tissue to be strong enough to withstand the optional manufacturing process. Additionally, the coating step 500 uniformly coats the outer part of the plant tissue. The coating step 500 prevents the plant tissue from having visual cosmetic inconsistencies including dull or matte outer tissue and small pockmarks resulting both from the saturating mix and the pressure of the dehydrating materials.

The coating mix may be composed of any of the saturating mixes set forth in FIG. 7. If a coating mix is used that involves the addition of a solvent 470, such as the silicone styrene elastomer resin mix 450, it is preferred that the ratio of the coating mix to solvent be varied depending on the type of plant tissue used. For example, if using more delicate plant tissue, it is preferred that the ratio be 1:1.25, meaning one part coating mix to one and a quarter parts solvent. If using stronger, thicker plant tissue, it is preferred that the ratio be 1:1, meaning one part coating mix to one part solvent.

It is preferred that the coating mix be applied to the plant tissue 510 for a total application time of approximately five seconds or less.

After applying the coating mix to the plant tissue, the plant tissue should preferably be removed and placed so that excess fluid still remaining and draining off the plant tissue pours, drips, or slides to the base of the plant tissue 570. This is advantageous because it helps reinforce the weaker areas of the plant tissue and in flowers prevents petals from falling off under conditions of extreme flexing. In particular, with orchids and flowers of similar physical construction, the draining of the solution as it dries is preferable because it helps reinforce the area of the petal that joins the stem to the flower. This step strengthens the small joints and connections of the flower against conditions of flexing. This helps the plant tissue to withstand manufacturing processes. After the excess coating mix is drained from the plant tissue 520, the plant tissue is then left to dry 530.

In a preferred method of draining 520 and subsequently drying 530 the plant tissue, the plant tissue is place on a rack to drain in the above stated manner, and routinely moved along various positions on the rack to ensure that the coating mix doesn't dry and stick to the rack.

The polishing step 600 which follows the application of the coating mix to the plant tissue, is shown in FIG. 8 and may be performed by the exemplary method shown. The polishing step 600 is optional, and its purpose is to provide aesthetically pleasing preserved plant tissue by creating a gloss on the surface of the plant tissue.

The polishing mix is applied to the plant tissue 610. The polishing mix is generally composed of a silicone styrene elastomer resin mix and solvent solution, wherein the weight of the solvent 470 generally outweighs that of the silicone styrene elastomer resin mix 450. The polishing mix may be an elastomer mix that is available commercially as "F-799™" 614 from Plasti Dip International of St. Paul, Minn.

The process of applying the polishing mix 610 should be very quick, because if the application lasts too long, the high percentage of solvents within the solution will dissolve the saturation mix and the coating mix. It is preferred that the application time be approximately five seconds or less.

After application of the polishing mix 610, the polishing mix is allowed to evaporate or drain off the outer part of the plant tissue 620, placed so that excess fluid still remaining and draining off the plant tissue pours, drips, or slides to the base of the plant tissue. It is then preferred that the plant tissue be left to dry 630 under ambient conditions until completely dry.

The optional manufacturing step 700 shown in FIGS. 1 and 2 takes the preserved plant tissue and manufactures the preserved plant tissue into permanently flexible high-wear applications under a wide range of temperature and humidity conditions. Some of the uses include attachments to and accessories for clothing, shoes, jewelry, purses, and hair accessories. The preserved plant tissue may also be used in other high-wear applications such as furniture, toys, pottery, dolls, dollhouse decorating, and embellishing decorative eggs.

The following examples further illustrate various methods used in the invention.

EXAMPLE 1

A plant tissue is formed and subsequently dehydrated by the basic burying method. After the plant tissue is formed, the container is kept at approximately 90° Fahrenheit for approximately 3 to 4 days, thereby removing essentially all moisture from the plant tissue.

EXAMPLE 2

A fibrous plant tissue, such as an orchid, is dehydrated by the microwaving dehydrating method. After the plant tissue is formed, the container is placed in and subsequently heated by a microwave oven for approximately 8 to 10 minutes. The container is then removed from the microwave oven and allowed to cool for approximately 4 hours, or until reaching room temperature. The plant tissue may then be conditioned by leaving the plant tissue in ambient conditions ranging between 60 to 70 percent humidity for approximately 24 hours. After the dehydrating materials are removed from the plant tissue by the chosen cleaning process, the plant tissue should be returned to a hot room at temperatures ranging between 90 to 100 degrees Fahrenheit and humidity ranging between 20 to 30 percent for not less than approximately 24 hours before being used in the saturation process. It may be retained in the recommended hot/dry conditions indefinitely before saturation of the plant tissue.

EXAMPLE 3

A dehydrated, fibrous plant tissue, such as an orchid or dogwood, is placed at a relative humidity of approximately 20 to 30 percent. A saturating mix is then applied to the plant tissue for approximately 30 minutes or more. After application of the saturating mix, the plant tissue is removed and placed so that excess fluid still remaining and draining from the plant tissue pours, drips, or slides to the base of the plant tissue. The plant tissue is then left to dry in ambient conditions, preferably between 55 to 65 degrees Fahrenheit and between 40 to 60 percent relative humidity, under which conditions it will take approximately two hours or more for the plant tissue to be dry to the touch and approximately five hours or more for the plant tissue to become completely dry.

A coating mix is subsequently applied to the plant tissue for a total application time of approximately five seconds or less. After application of the coating mix, the plant tissue is allowed to dry in ambient conditions, preferably between 55 to 65 degrees Fahrenheit and between 40 to 60 percent relative humidity, under which conditions it will take approximately two hours for the plant tissue to be dry to the touch and approximately five or six hours for the plant tissue to become completely dry.

EXAMPLE 4

A small, thinly textured plant tissue, such as a rose, is placed at a relative humidity of approximately 20–30 percent. The plant tissue is saturated with a saturating mix for approximately more than one minute. After application of the saturating mix, the plant tissue is removed and placed so that excess fluid still remaining and draining from the plant tissue pours, drips, or slides to the base of the plant tissue. The plant tissue is then left to dry in ambient conditions, preferably between 55 to 65 degrees Fahrenheit and between 40 to 60 percent relative humidity, under which conditions it will take approximately two hours or more for the plant tissue to be dry to the touch and approximately five hours or more for the plant tissue to become completely dry.

A coating mix is then applied to the plant tissue for a total application time of approximately five seconds or less. After application of the coating mix, the plant tissue is allowed to dry in ambient conditions, preferably between 55 to 65 degrees Fahrenheit and between 40 to 60 percent relative humidity, under which conditions it will take approximately two hours for the plant tissue to be dry to the touch and approximately five or six hours for the plant tissue to become completely dry.

The terms and expressions that have been employed in the foregoing specification are used as terms of description, not of limitation, and are not intended to exclude equivalents of the features shown and described or portions of them. The scope of the invention is defined and limited only by the claims that follow.

What is claimed is:

1. A method for preserving plant tissue, said method comprising the steps of:
   (a) obtaining a dehydrated plant tissue; and
   (b) saturating said plant tissue with a saturation mix, said saturation mix composed of a silicone styrene elastomer resin mix,
   (c) wherein said silicone styrene elastomer resin mix is selected from the group consisting of:
      (i) copolymers of dimethylsiloxane and polystyrene;
      (ii) block copolymers of dimethylsiloxane and polysterene;
      (iii) copolymers of dimethylsiloxane and polystyrene mixed with a rubber vulcanizing agent;
      (iv) copolymers of dimethylsiloxane and polystyrene mixed with an antioxidant; and
      (v) copolymers of dimethylsiloxane and polystyrene mixed with a UV stabilizer.

2. The method of claim 1, said method further comprising the step of:
   (a) applying a coating mix to said saturated plant tissue.

3. The method of claim 2, further comprising:
   (a) applying a polishing mix to said coated plant tissue.

4. The method of claim 3, said step of applying a polishing mix to said coated plant tissue further comprising the steps of:
   (a) draining said polished plant tissue; and
   (b) drying said polished plant tissue.

5. The method of claim 3, wherein said polishing mix is composed of a silicone styrene elastomer resin mix.

6. The method of claim 1, said step of obtaining a dehydrated plant tissue comprising:
   (a) obtaining a fresh-cut plant tissue;
   (b) forming said fresh-cut plant tissue; and
   (c) dehydrating said fresh-cut plant tissue.

7. The method of claim 6, wherein said step of dehydrating said fresh cut plant tissue comprises at least one method selected from the group consisting of:
   (a) burying dehydrating method;
   (b) burying and sealing dehydrating method;
   (c) hang-drying dehydrating method;
   (d) microwaving dehydrating method;
   (e) chemical dehydrating method; and
   (f) freeze-drying dehydrating method.

8. The method of claim 1, further comprising a cleaning step comprising at least one step selected from the group consisting of:
   (a) vibrating said plant tissue to remove said dehydrating material;
   (b) air-brushing said plant tissue to remove said dehydrating material; and
   (c) brushing said plant tissue to remove said dehydrating material.

9. The method of claim 1, said step of saturating said plant tissue with said saturation mix further comprising the steps of:
   (a) draining said saturation mix from said saturated plant tissue; and
   (b) drying said saturated plant tissue.

10. The method of claim 1, said step of coating said plant tissue further comprising the steps of:
    (a) applying a coating mix to said saturated plant tissue;
    (b) draining said coating mix from said coated plant tissue; and
    (c) drying said coated plant tissue.

11. The method of claim 2, wherein said coating mix is composed of at least one mix selected from the group consisting of:
    (a) solution composed of derivatives of natural rubber;
    (b) natural rubber solution;
    (c) any solution imparting a rubber-like flexibility; and
    (d) a silicone styrene elastomer resin mix.

12. The method of claim 1, further comprising a step of adding said silicone styrene elastomer resin mix to a solvent, said solvent selected from the group consisting of:
    (a) toluene;
    (b) xylene;
    (c) naphtha;

(d) acetone; and (e) various combinations of elements of (a)–(d).

13. A method for preserving plant tissue, said method comprising the steps of:
  (a) obtaining a dehydrated plant tissue;
  (b) saturating said plant tissue with a saturation mix;
  (c) said saturation mix being composed of a silicone styrene elastomer resin mix; and
  (d) said silicone styrene elastomer resin mix comprises one or more copolymers of dimethylsiloxane and polystyrene.

14. The method of claim 13, said step of saturating said plant tissue with said saturation mix further comprising the steps of:
  (a) draining said saturation mix from said saturated plant tissue; and
  (b) drying said saturated plant tissue.

15. The method of claim 14, further comprising the step of applying a coating mix to said saturated plant tissue, said step of applying a coating mix further comprising the steps of:
  (a) applying a coating mix to said saturated plant tissue;
  (b) draining said coating mix from said coated plant tissue; and
  (c) drying said coated plant tissue.

* * * * *